United States Patent [19]

Tsukada

[11] Patent Number: 5,800,170

[45] Date of Patent: Sep. 1, 1998

[54] INTERNAL POLLUTION PREVENTING APPARATUS FOR HANDPIECE

[75] Inventor: Yoshiro Tsukada, Oome, Japan

[73] Assignee: Hinatawada Seimitu Mfg. Co., Ltd., Oome, Japan

[21] Appl. No.: 691,883

[22] Filed: Aug. 1, 1996

[30] Foreign Application Priority Data

Nov. 2, 1995 [JP] Japan .................. 7-309929

[51] Int. Cl.⁶ .................................................. A61C 1/02
[52] U.S. Cl. ................................................... 433/98
[58] Field of Search ........................ 433/98, 101, 82, 433/84

[56] References Cited

U.S. PATENT DOCUMENTS

| | | | |
|---|---|---|---|
| 3,237,306 | 3/1966 | Staunt | 433/84 |
| 4,443,195 | 4/1984 | Matsui | 433/98 |
| 4,797,098 | 1/1989 | Kawata | 433/98 |
| 5,295,829 | 3/1994 | Frey et al. | 433/98 X |
| 5,464,350 | 11/1995 | Bierbaum | 433/84 |

FOREIGN PATENT DOCUMENTS 1817520  3/1980  Germany .................. 433/98

*Primary Examiner*—Nicholas D. Lucchesi
*Attorney, Agent, or Firm*—McGlew and Tuttle

[57] ABSTRACT

The invention provides an internal pollution preventing apparatus for a handpiece wherein a valve itself is small and compact and a housing is small in size and which is small in number of parts and superior in assembling facility, airtightness and economy.

The apparatus has an air turbine drive air circuit A for supplying, when the handpiece operates, air of a comparatively high pressure via a valve 1, an exhaust air circuit D for exhausting air after having driven an air turbine of the handpiece, a chip air circuit B for supplying air for the atomization of cooling water via valves V1, V2, V3, V4 and V5, and a low pressure air feeding circuit E for feeding air turbine stopping and circuit internal pressure keeping air of a low pressure to the drive air circuit and the chip air circuit via further valves. An exhausting change-over valve V6 for opening and closing the exhaust air circuit with respect to the atmospheric air is provided in the exhaust air circuit D in such a manner as to be directly opened or closed by a pilot pressure in the drive air circuit A or the chip air circuit B. The apparatus is characterized in that each valve is formed in a mushroom shape.

2 Claims, 3 Drawing Sheets

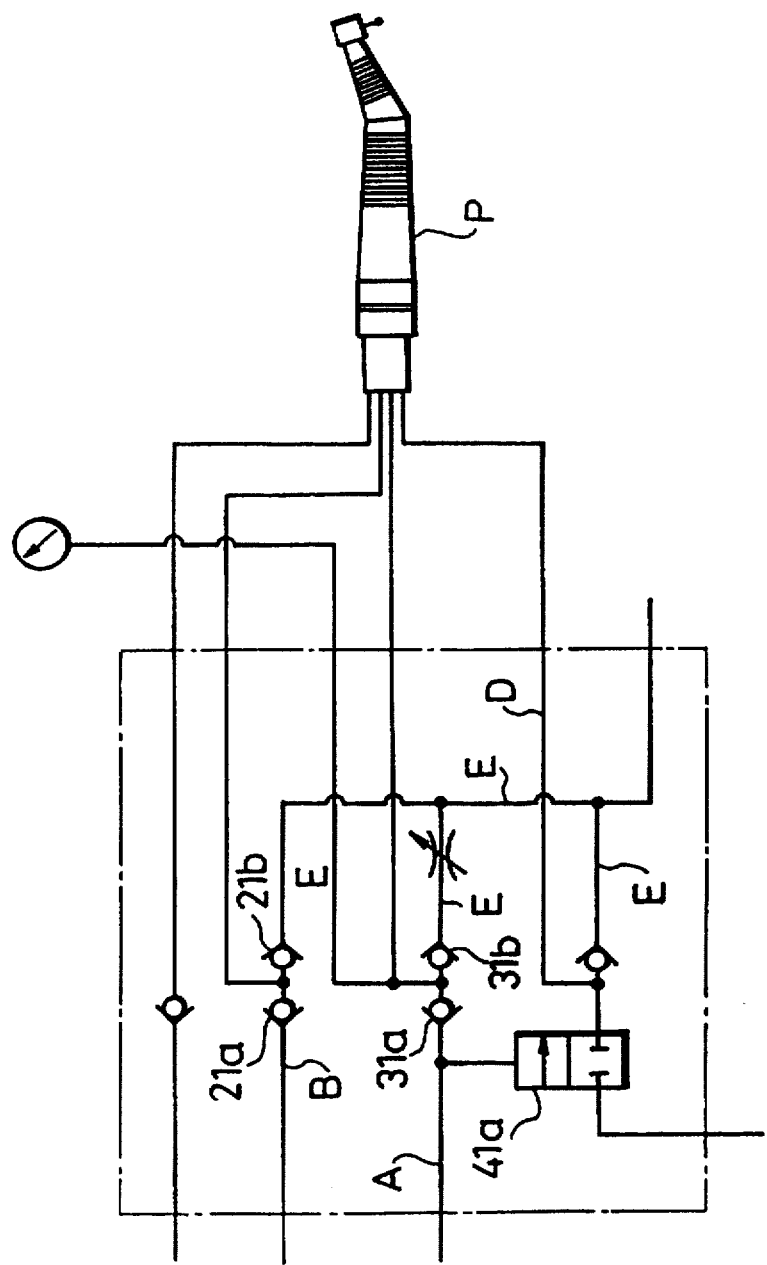

INTERNAL POLLUTION PREVENTING APPARATUS FOR HANDPIECE

BACKGROUND OF THE INVENTION

This invention relates to an apparatus for preventing internal pollution of an air turbine handpiece for the dental therapy used to drill a tooth and an operating mechanism for the air turbine handpiece.

In an air turbine handpiece for the dental therapy which has been conventionally put to practical use, an air flow of a high pressure (2 to 4 kg/cm$^2$) from an external compressed air supply source is applied through an air supply pipe to air receiving blades of an air turbine provided at an end of the handpiece and is exhausted through an exhaust pipe to rotate the air turbine at a high speed (approximately 400,000 revolutions per minute) to drive a drill directly connected with the turbine.

Further, in order to prevent a temperature rise of the drill by heat generated during use of the handpiece and wash away waste from a tooth, cooling water supplied from an external water supply source is jetted toward the extremity of the drill through a water pipe while air is jetted from a chip air nozzle provided in a juxtaposed relationship with the water jet nozzle to atomize the cooling water.

By the way, with a handpiece on which a drill revolves at high speed during the therapy of the mouth, in order to prevent a possible danger arising from inadvertent contact of the drill with a membrane of the buccal cavity when the handpiece is taken out of the mouth upon completion of the therapy or the like, it is made a habit to take out the handpiece from the mouth after the supply of air to the air turbine is stopped at the working position of the handpiece and it is confirmed that the revolution of the drill has stopped.

However, even if the supply of driving air to the air turbine revolving at high speed is stopped, the air receiving blades of the air turbine continue to revolve for a little while due to their inertia, and consequently, a phenomenon wherein the inside of the structure of the handpiece is brought to a negative pressure arises.

As a result, cooling water sticking to a drill chucking portion or some other structural gap portion may possibly be sucked as filthy water containing waste of a tooth, saliva, blood or various bacteria into the inside of the structure of the handpiece through the end of the handpiece held at the working position and may thus cause internal pollution of the handpiece.

Further, the internal pollution caused by the negative pressure phenomenon comes up to an air supply pipe, an exhaust pipe, a chip air pipe and a water supply pipe connected to the handpiece and sometimes comes up further to the mechanism section for controlling the supply and the exhaust of driving air and water.

Consequently, even if only the air turbine at the end of the handpiece is removed from the structure section and disinfected after completion of an operation, if the handpiece connected to the pipes mentioned above is used to supply air and water into the handpiece upon subsequent therapy, the inside of the air turbine becomes polluted again from the supply sides of air and water, which makes futile the preceding disinfection of the turbine.

From the situations described above, effective disinfection of a handpiece of the type described above is impossible except to prevent internal pollution of the handpiece beforehand.

Therefore, the inventor of the present invention has developed an internal pollution preventing apparatus for a handpiece as means for preventing such internal pollution of a handpiece. The internal pollution preventing apparatus is disclosed in Japanese Utility Model Publication Application No. Heisei 6-20492 and is constructed such that the internal pressure of the handpiece is set, upon completion of an operation, to and thereafter kept at a positive pressure so that admission of foreign elements such as bacteria from the outside is hindered.

DESCRIPTION OF FIGURES

The internal pollution preventing apparatus mentioned above incudes such circuits as shown in FIG. 5. In particular, referring to FIG. 5, the internal pollution preventing apparatus has an air turbine drive air circuit A for supplying, when the handpiece operates, air of a comparatively high pressure via a valve 31a, an exhaust air circuit D for exhausting air after the air turbine is driven, a chip air circuit B for supplying air for the atomization of cooling water via a valve 21a, and a low pressure air feeding circuit E for feeding air during turbine stopping and for maintaining circuit internal pressure keeping, to keep air of a low pressure via valves 21b and 31b provided to the circuits A and B, respectively. The internal pollution preventing apparatus includes an exhausting change-over valve 41a provided in the exhaust air circuit D for opening or closing the exhaust air circuit D with respect to the atmospheric air. The change-over valve 41a is directly opened or closed by a pilot pressure of the drive air circuit A or the chip air circuit B. In this instance, each of the valves 21a, 21b, 31a and 31b is composed of a spring and a piston valve normally urged in the closing direction by the spring.

In the apparatus described above, if air is supplied into the drive air circuit A and the chip air circuit B, then the valves 21a and 31a in the circuits are opened, and the valves on the low pressure air feeding circuit side are closed, so that air is fed to the handpiece P side to drive the air turbine and jet cooling water. In this instance, the change-over valve 41a in the exhaust air circuit is opened by the pilot pressure of the drive air circuit A or the chip air circuit B, so that the air which has driven the air turbine is exhausted into the atmospheric air.

Figure 1:
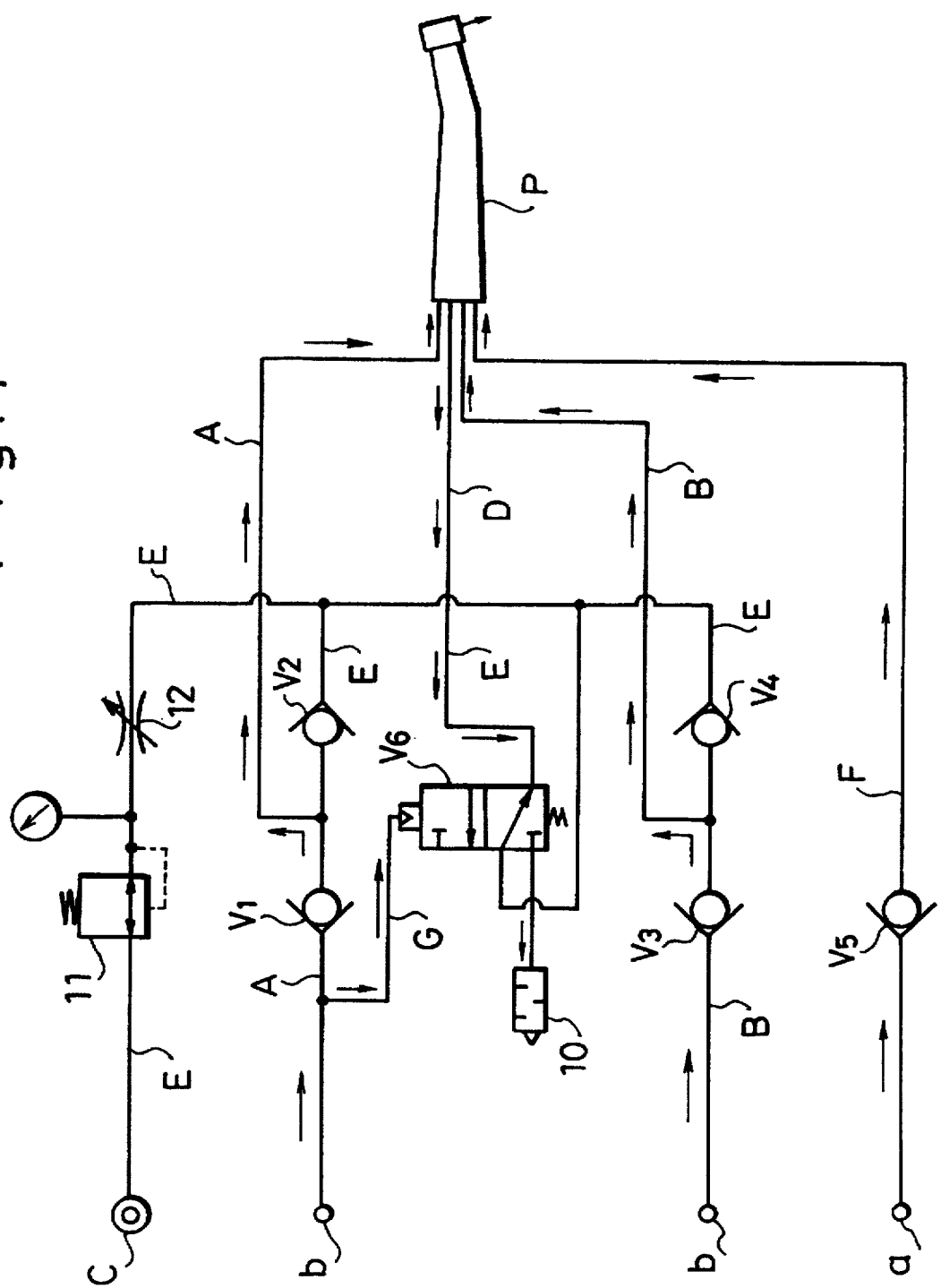

If the supply of air to the drive air circuit A and the chip air circuit B is stopped while air is supplied to the low pressure circuit, then the valves 21b and 31b on the low pressure air feeding circuit side are opened, so that low pressure air is supplied into the drive air circuit A, the chip air circuit B and the exhaust air circuit D. In this instance, the valves 21a and 31a in the drive air circuit A and the chip air circuit B are closed while low pressure air is supplied to the handpiece side.

Further, if the supply of air to the drive air circuit A and the chip air circuit B is stopped, then the change-over valve 41a is closed. Consequently, air from the low pressure air feeding circuit E supplied into the exhaust air circuit D is supplied to the handpiece P side, so that the air turbine is stopped and the insides of the handpiece and the circuits are thereafter kept at a positive pressure.

However, although the apparatus described above operates well, since each of the valves 21a, 31a and so forth is composed of a spring and a piston valve, the apparatus is disadvantageous in that it is complicated in structure, comparatively great in number of parts, large in size of an overall housing, difficult in working and assembly and high in production cost. Further, where any circuit is opened or closed with the piston valve, the control of accuracy for assuring the airtightness is difficult. Thus, there is another problem that to raise the accuracy of the device, a higher working cost is required.

SUMMARY OF THE INVENTION

It is an object of the present invention to provide an internal pollution preventing apparatus for a handpiece wherein a valve itself is small and compact and a housing is small in size and which is small in number of parts and superior in assembling facility, airtightness and economy.

In order to attain the object described above, according to the present invention, an internal pollution preventing apparatus for a handpiece which has an air turbine drive air circuit for supplying, when the handpiece operates, air of a comparatively high pressure via a valve, an exhaust air circuit for exhausting air after having driven an air turbine of the handpiece, a chip air circuit for supplying air for the atomization of cooling water via another valve, and a low pressure air feeding circuit for feeding air turbine stopping and circuit internal pressure keeping air of a low pressure to the drive air circuit and the chip air circuit via further valves, and wherein an exhausting change-over valve for opening and closing the exhaust air circuit with respect to the atmospheric air is provided in the exhaust air circuit in such a manner as to be directly opened or closed by a pilot pressure in the drive air circuit or the chip air circuit, is characterized in that each of the valves is formed in a mushroom shape.

Preferably, each of the mushroom-shaped valves has a valve body having an upper face curved in a convex condition and a flat lower face, a post-like supporting leg portion extending from the center of the lower face of the valve body, and a stopper provided substantially at a middle portion of the supporting leg portion, and the valve body has a central reinforcing portion of a comparatively great thickness, and a resilient lip integrally provided continuously with an outer periphery of the reinforcing portion. Further preferably, each of the drive air circuit, the chip air circuit and the low pressure air feeding circuit has a partition plate provided intermediately thereof, and the partition plate has one or a plurality of through-holes formed therein while the supporting leg portion of a corresponding one of the mushroom-shaped valves is inserted in another hole formed in the partition plate and the mushroom-shaped valve is held by the stopper thereof such that the lip is closely contacted for opening and closing movement with the exit side of the through-holes.

BRIEF DESCRIPTION OF THE DRAWINGS

Figure 2:
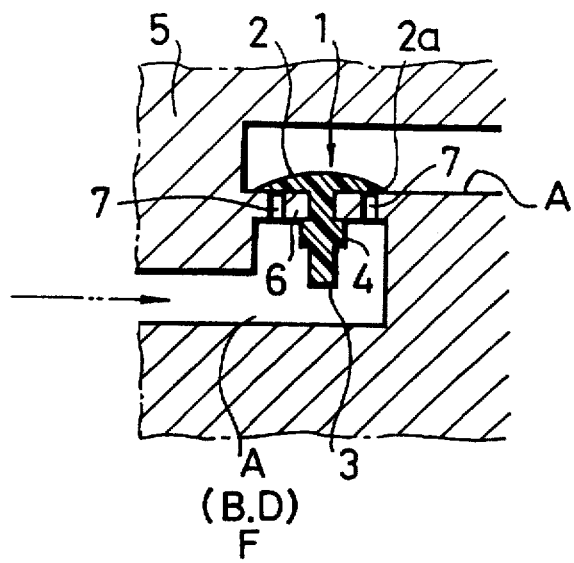
Figure 3:
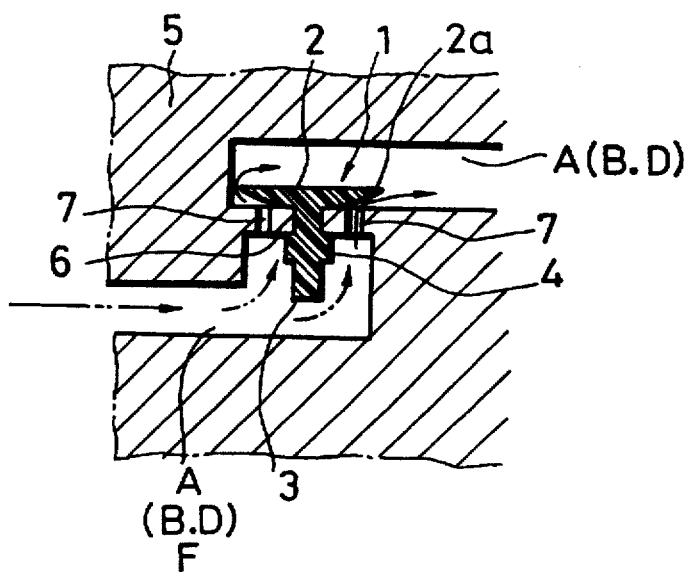
Figure 4:
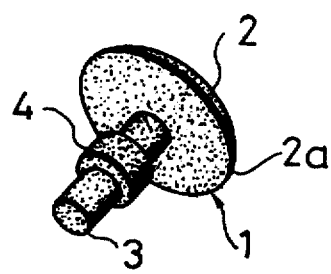

FIG. 1 is a circuit diagram of a pneumatic circuit of an internal pollution preventing apparatus for a handpiece to which the present invention is applied;

FIG. 2 is a sectional view of a valve in the circuit of FIG. 1 when the valve is in a closed condition;

FIG. 3 is a similar view but showing the valve of FIG. 2 in an open condition;

FIG. 4 is a perspective view showing the valve of FIG. 2; and

FIG. 5 is a circuit diagram of a pneumatic circuit of a conventional internal pollution preventing apparatus for a handpiece.

DESCRIPTION OF THE PREFERRED EMBODIMENT

The present invention is described below with reference to the drawings. FIG. 1 shows a pneumatic circuit where an internal pollution prevention apparatus for a handpiece of the present invention is incorporated in a housing body.

A high pressure air feeding source b is connected to a handpiece P via a drive air circuit A and a check valve V1.

Similarly, the high pressure air feeding source b is connected to the handpiece P also via a chip air circuit B and a check valve V3.

A water supply source a is connected to the handpiece P via a water supply circuit F and a check valve V5.

The handpiece P is communicated with the atmospheric air via an exhaust air circuit D and a change-over valve V6. Consequently, air supplied from the drive air circuit A drives an air turbine of the handpiece P and is discharged to the atmospheric air through the exhaust air circuit D.

On the other hand, a low pressure air feeding source C is connected to low pressure air feeding circuits E, one of which is connected to the drive air circuit A via a check valve V2 and another one of which is connected to the exhaust air circuit D via the change-over valve V6. Consequently, when the handpiece P is inoperative, low pressure air is supplied from the low pressure air feeding source C through the low pressure air feeding circuits E and pushes open the check valves V2, V4 and V6 so that it is supplied to the drive air circuit A, the chip air circuit B and the exhaust air circuit D simultaneously to stop the driving of the air turbine and set and thereafter keep the internal pressures of the handpiece P and the circuits set and at a positive pressure.

The valves, that is, the check valves V1, V2, V3 and V5, are each molded in a mushroom shape with rubber, synthetic resin or the like as shown in FIGS. 2, 3 and 4.

Referring to FIGS. 2, 3 and 4, the mushroom-shaped valve 1 has a circular valve body 2 having an upper face curved in a convex condition and a flat lower face, a post-like supporting leg portion 3 extending downwardly from the center of the lower face of the valve body 2, and a ring-shaped stopper 4 provided substantially at a middle portion of the supporting leg portion 3. The valve body 2 has a central reinforcing portion of a comparatively great thickness, and a resilient lip 2a integrally provided continuously to an outer periphery of the reinforcing portion.

The drive air circuit A, the chip air circuit B and the low pressure air feeding circuits E are formed in a housing 5, and a partition plate 6 is provided intermediately in each of the circuits of the housing 5. Each of the partition plates 6 has one or a plurality of through-holes 7 formed therein, and the supporting leg portion 3 is inserted in another hole of the partition plate 6 and the valve 1 is held on the partition plate 6 by the stopper 4 thereof while the lip 2a is closely contacted for opening and closing motion with the face of the partition plate 6 on the exit side of the through-holes 7. Consequently, if air is supplied in the direction of an arrow mark, the air is fed through the through-holes 7 to the handpiece P side pushing open the lip 2a as seen in FIG. 3.

With the internal pollution preventing apparatus for a handpiece having the construction described above, pressurized water from the water supply source a pushes open the check valve V5 and is sent out toward a water pipe at an end of the handpiece P.

Simultaneously, compressed air from the water supply source a for high pressure air is introduced into the drive air circuit A and the chip air circuit B, in which the check valves V1 and V3 of the two circuits are pushed open by the pressure of the compressed air, so that the compressed air is fed toward the air turbine of the handpiece P side while chip air is sent out toward a chip air pipe of the handpiece P side.

Besides, the air supplied into the drive air circuit A branches into a valve control circuit G, so that it pushes open the change-over valve V6 to the upper port side.

In each of the other check valves V2 and V6 in the drive air circuit A and the chip air circuit B, the pressure acts upon the valve body 2 side to urge the lip 2a in its closing direction. Consequently, the through-holes 7 are kept in the closed positions by the lip 2a.

As a result, after a large amount of compressed air of a comparatively high pressure comes to and drives the air turbine of the handpiece P to drive the drill mounted on the handpiece P, it is exhausted into the external air from a silencer 10 via the exhaust air circuit D and the change-over valve V6 which is in an open condition.

By this operation, at the end of the handpiece P, the drill which is driven by the air turbine is revolved at high speed while cooling water is simultaneously jetted toward the drill and is atomized by chip air. Consequently, a therapeutic operation can be performed while the drilling face is cooled and waste material of the tooth is washed out.

If the supply of cooling water and high pressure drive air as well as chip air is stopped simultaneously with completion of the therapeutic operation, then the check valve V5 in the water supply circuit for cooling water is closed by the restoring force of the lip 2a thereof, and also the check valves V1 and V3 in the drive air circuit A and the chip air circuit B are closed similarly. Further, as the pilot pressure of the valve control circuit G is lost, the change-over valve V6 is changed over to the lower side port, so that the exhaust air circuit D is connected to the low pressure air feeding circuit E.

Then, in the two air circuits A and B, the internal pressures drop as a result of the stopping of the supply pressure, and the other check valves V2 and V4 are opened by a comparatively low feeding air pressure provided thereto from the low pressure air feeding circuit E. Consequently, the air supplied to the handpiece P is changed over in a moment from air of a high pressure to air of a low pressure.

Namely, if supply of air to the drive air circuit A or the chip air circuit B is stopped, then air of a low pressure from the low pressure air feeding circuit E is introduced from a pressure reducing valve 11 and a flow control valve 12 to the drive air circuit A, the chip air circuit B and the exhaust air circuit D via the check valves V2 and V4 and the change-over valve V6, respectively, whereafter it is fed to the handpiece P. Consequently, the internal pressure of the handpiece P is thereafter kept at a positive pressure, and as a result, admission of polluting substances or bacteria is prevented.

In this manner, with the internal pollution preventing apparatus for a handpiece according to the present invention, since air of a low pressure is supplied, upon stopping of an operation, into the circuits and the handpiece, the air turbine is stopped and the internal pressures of the circuits and the handpiece are kept at a positive pressure, and consequently, admission of external soil, bacteria and so forth can be prevented.

Further, since the valve is formed in a mushroom shape, the valve itself is a unitary member and can be formed with a small size. Consequently, the valve has a good responsibility and is superior in workability and assembling facility and easy to manage the accuracy. Further, the valve is small and compact in overall structure and improved very much in economy. Since the valve body forming the valve is composed of a central reinforcing portion of a comparatively great thickness and a resilient lip integrally provided continuously to an outer periphery of the reinforcing portion, the lip of the valve body itself is improved in durability since it is reinforced by the reinforcing portion, and also the responsibility of the lip in opening and closing operation is good.

What is claimed is:

1. An internal pollution preventing apparatus of a handpiece, comprising:

an air turbine drive air circuit for supplying, when said handpiece operates, air of a comparatively high pressure via a valve;

an exhaust air circuit for exhausting air after the air has driven an air turbine of the handpiece;

a chip air circuit for supplying air for the atomization of cooling water via another valve;

a low pressure air feeding circuit for feeding turbine stopping air and feeding circuit internal pressure maintaining air, of a low pressure, to said drive air circuit and to said chip air circuit via further valves;

an exhausting change-over valve for opening and closing said exhaust air circuit with respect to the atmospheric air, said exhausting change-over valve being provided in said exhaust air circuit so as to be directly opened or closed by a pilot pressure in said drive air circuit or said chip air circuit, each of said valve, said another valve and said further valves being formed in a mushroom shape with a valve body having an upper face curved in a convex condition and a flat lower face, a post-like supporting leg portion extending from the center of the lower face of said valve body, and a stopper provided substantially at a middle portion of said supporting leg portion, said valve body having a central reinforcing portion of a comparatively great thickness, and a resilient lip integrally provided continuously with an outer periphery of said reinforcing portion.

2. The internal pollution preventing apparatus as claimed in claim 1, wherein each of said drive air circuit, said chip air circuit and said low pressure air feeding circuit has a partition plate provided intermediately thereof, said partition plate having one or a plurality of through-holes formed therein, a said supporting leg portion of a corresponding one of said mushroom-shaped valves being inserted in another hole formed in said partition plate, said one of said mushroom-shaped valves being held by said stopper such that said lip is in close contact for opening and closing movement with an exit side of said through-holes.

* * * * *